US007800086B2

(12) United States Patent
Ziener et al.

(10) Patent No.: US 7,800,086 B2
(45) Date of Patent: Sep. 21, 2010

(54) ARRANGEMENT FOR RADIATION GENERATION BY MEANS OF A GAS DISCHARGE

(75) Inventors: Christian Ziener, Jena (DE); Guido Hergenhan, Grossloebichau (DE); Frank Flohrer, Jena (DE); Juergen Kleinschmidt, Goettingen (DE)

(73) Assignee: Xtreme technologies GmbH, Goettingen (DE)

( * ) Notice: Subject to any disclaimer, the term of this patent is extended or adjusted under 35 U.S.C. 154(b) by 1071 days.

(21) Appl. No.: 11/464,887

(22) Filed: Aug. 16, 2006

(65) Prior Publication Data

US 2007/0040511 A1 Feb. 22, 2007

(51) Int. Cl.
*A61N 5/06* (2006.01)

(52) U.S. Cl. ............................ 250/504 R; 315/111.21; 372/76; 372/81; 372/82

(58) Field of Classification Search ............ 250/504 R, 250/493.1, 503.1; 315/111.21, 111.81; 372/76, 372/81, 82, 86–88
See application file for complete search history.

(56) References Cited

U.S. PATENT DOCUMENTS

| | | | | |
|---|---|---|---|---|
| 7,154,109 | B2 * | 12/2006 | Stivers | 250/504 R |
| 7,427,766 | B2 * | 9/2008 | Jonkers et al. | 315/111.21 |
| 7,501,642 | B2 * | 3/2009 | Moors et al. | 250/504 R |

FOREIGN PATENT DOCUMENTS

| | | |
|---|---|---|
| DE | 103 42 239 | 6/2005 |
| EP | 1 401 248 | 3/2004 |
| RU | 2252496 | 1/2004 |
| WO | 2005/025280 | 3/2005 |

OTHER PUBLICATIONS

J. Phys. D: Appl. Phys. 37 (2004) 3254-3265 "EUV sources using Xe and Sn discharge plasmas" Vladimir M. Borisov, et al.
State Research Center of Russian Federation Troitsk Institute for Innovation and Fusion Research (TRINITI), 3$^{rd}$ Int'l EUVL Symposium, Nov. 1-4, 2004 Japan Power Scaling of DPP Source for EUV Lithography: Xe or SN?* V. Borisov.

* cited by examiner

*Primary Examiner*—Douglas W Owens
*Assistant Examiner*—Ephrem Alemu
(74) *Attorney, Agent, or Firm*—Frommer Lawrence & Haug LLP

(57) ABSTRACT

An arrangement for the generation of radiation by a gas discharge has the object of achieving a considerable reduction in the inductance of the discharge circuit for the gas discharge while simultaneously increasing the lifetime of the electrode system. Also, the use of different emitters is ensured. A rotary electrode arrangement accommodated in the discharge chamber contains electrodes which are rigidly connected to one another at a distance from one another and are mounted so as to be rotatable around a common axis. Capacitor elements of a high-voltage power supply for generating high-voltage pulses for the two electrodes are arranged in a free space formed by the mutual distance. The electrodes are electrically connected to the capacitor elements and to a voltage source for charging the capacitor elements.

24 Claims, 6 Drawing Sheets

ARRANGEMENT FOR RADIATION GENERATION BY MEANS OF A GAS DISCHARGE

CROSS-REFERENCE TO RELATED APPLICATION

This application claims priority of German Application No. 10 2005 039 849.9, filed Aug. 19, 2005, the complete disclosure of which is hereby incorporated by reference.

BACKGROUND OF THE INVENTION a) Field of the Invention

The invention is directed to an arrangement for generating radiation by means of a gas discharge containing a discharge chamber, which has a discharge area for the gas discharge for forming a plasma that emits the radiation from a starting material and an emission opening for the generated radiation, a first electrode and a second electrode which are mounted so as to be rotatable, and a high-voltage power supply for generating high-voltage pulses between the two electrodes.

b) Description of the Related Art

Radiation sources which are based on plasmas generated by gas discharge and which rely on various concepts have already been described many times. The principle common to these arrangements consists in that a pulsed high-current discharge of more than 10 kA is ignited in a gas of determinate density, and a very hot (kT>20 eV) and dense plasma is generated locally as a result of the magnetic forces and the dissipated power in the ionized gas.

It is particularly important to prolong the life of the source components because exchanging them causes downtimes in production facilities in which the radiation sources are employed.

In radiation sources based on a gas discharge, it is principally the electrode system, in particular the electrodes, that is subject to extensive wear caused by heating and erosion. While the heating of the electrodes is brought about chiefly by the flow of current through the electrodes and by the radiation of the plasma, fast particles exiting from the radiation-emitting plasma lead to erosion.

Known solutions corresponding to WO 2005/025280 A2 and RU 2 252 496 C2 use rotating electrodes in order to counter the heating of the electrodes.

In the arrangement disclosed in WO 2005/025280 A2 which is suitable for metal emitters, the rotating electrodes also dip into a vessel containing molten metal, e.g., tin, wherein the metal applied to the electrode surface is vaporized by laser radiation, and the vapor is ignited by a gas discharge to form a plasma.

WO 2005/025280 A2 further proposes conveying the current pulse to the electrodes by means of the molten metal in that the capacitors needed for storing the electrical energy for plasma generation are electrically connected to the liquid metal in the vessels by means of a plurality of metal pins or bands which are embedded in a vacuum-tight manner in insulators. Since the capacitors are arranged outside of the discharge chamber, this inevitably leads to a high inductance in the discharge circuit due to the required current feedthroughs to the electrodes. This lengthens the duration of the current pulses through the electrodes so that the energy that can be deposited in the plasma cannot be used efficiently for generation of radiation.

OBJECT AND SUMMARY OF THE INVENTION

Therefore, it is the primary object of the invention to achieve a considerable reduction in the inductance of the discharge circuit for the gas discharge while simultaneously increasing the lifetime of the electrode system. Also, the use of different emitters is ensured.

According to the invention, this object is met by an arrangement for generating radiation by means of a gas discharge of the type mentioned above in that the electrodes are rigidly connected to one another at a distance from one another and are mounted so as to be rotatable around a common axis, wherein capacitor elements of the high-voltage power supply are arranged in a free space formed by the mutual distance, and in that the electrodes are electrically connected to the capacitor elements and to a voltage source for charging the capacitor elements.

The inductance of the discharge circuit is considerably reduced in that the capacitor elements needed for storing the electrical energy are arranged between the jointly rotating electrodes and in that they have a direct electrical connection to the electrodes. This ensures a very fast rise of the current during the discharge and leads to an increased conversion efficiency of electrical energy to emitted radiation energy. The capacitor elements can be charged either by DC current or by short current pulses.

In a special development of the invention, the electrodes are immersed in baths of molten metal which are electrically separated from one another, so that the surface of the electrodes is wetted by the metal during the rotation of the electrodes.

Alternatively, the electrodes can come into electrical contact with immersion elements which are oriented coaxial to the axis of rotation and which penetrate into the melt baths which are electrically separated from one another.

In both constructions, the electrical connection of the electrodes to the voltage source is carried out by means of the melt baths, wherein a tin bath or a lithium bath can be provided as molten metal.

According to another construction of the arrangement according to the invention, the molten metal picked up by the electrodes serves as a starting material for generating radiation.

Alternatively, an injection device can also be directed to the discharge area, which injection device provides a series of individual volumes of the starting material serving to generate radiation as liquid droplets or solid droplets and injects them into the discharge area at a distance from the electrodes.

In the arrangement according to the invention, by which in particular extreme ultraviolet radiation can be generated through a gas discharge, the injection of individual volumes ensures a maximum distance between the location of the plasma generation and the electrodes.

In connection with the rotation of the electrodes, the step employed for increasing distance in which the starting material that is provided as the emitter for the generation of radiation is placed at an optimal location for plasma generation in dense state as a droplet or globule and is pre-ionized therein results in an increased lifetime of the electrodes. Further, limitations regarding the emitter material itself can be eliminated so that xenon and tin, as well as tin compounds or lithium, can also be used. By dense state is meant solid-state density or a density of a few orders of magnitude below solid-state density.

According to the invention, the optimal quantity of emitters for the desired radiation emission in the EUV wavelength range per discharge pulse is determined by the size of the injected individual volumes virtually independent of the background gas density. In this sense, the starting material serving as emitter is supplied in a regenerative and genuinely mass-limited form.

Another advantage in supplying the emitter material in the form of small individual volumes through a injection device consists in the possibility of introducing droplets of emitter material at a desired location within the range of the electrodes. In this way, it is possible to realize a radiation source that emits radiation in any desired direction.

It is particularly advantageous when an energy beam provided by an energy beam source is directed to the starting material for the generation of radiation so that an at least partial pre-ionization of the starting material is carried out which ensures that the discharge energy is coupled into the starting material in an optimal manner. Further, the geometry of the electrodes can be appreciably expanded compared with the exclusive use of; preferably, argon as background gas.

Laser beam sources, electron beam sources or ion beam sources are suitable as energy beam sources.

A device which is arranged in the free space between the electrodes, particularly between the discharge area and the capacitor elements, and which comprises a labyrinth seal of electrically insulating or metallic cylinder rings which are arranged in an alternating manner at the electrodes, overlap at least partially, and surround the capacitor elements serves to prevent unwanted material deposits at the electrodes, at the capacitors or at the arrangements ensuring the spacing of the electrodes.

The invention will be described more fully in the following with reference to the schematic drawings.

DESCRIPTION OF THE PREFERRED EMBODIMENTS

Figure 1:
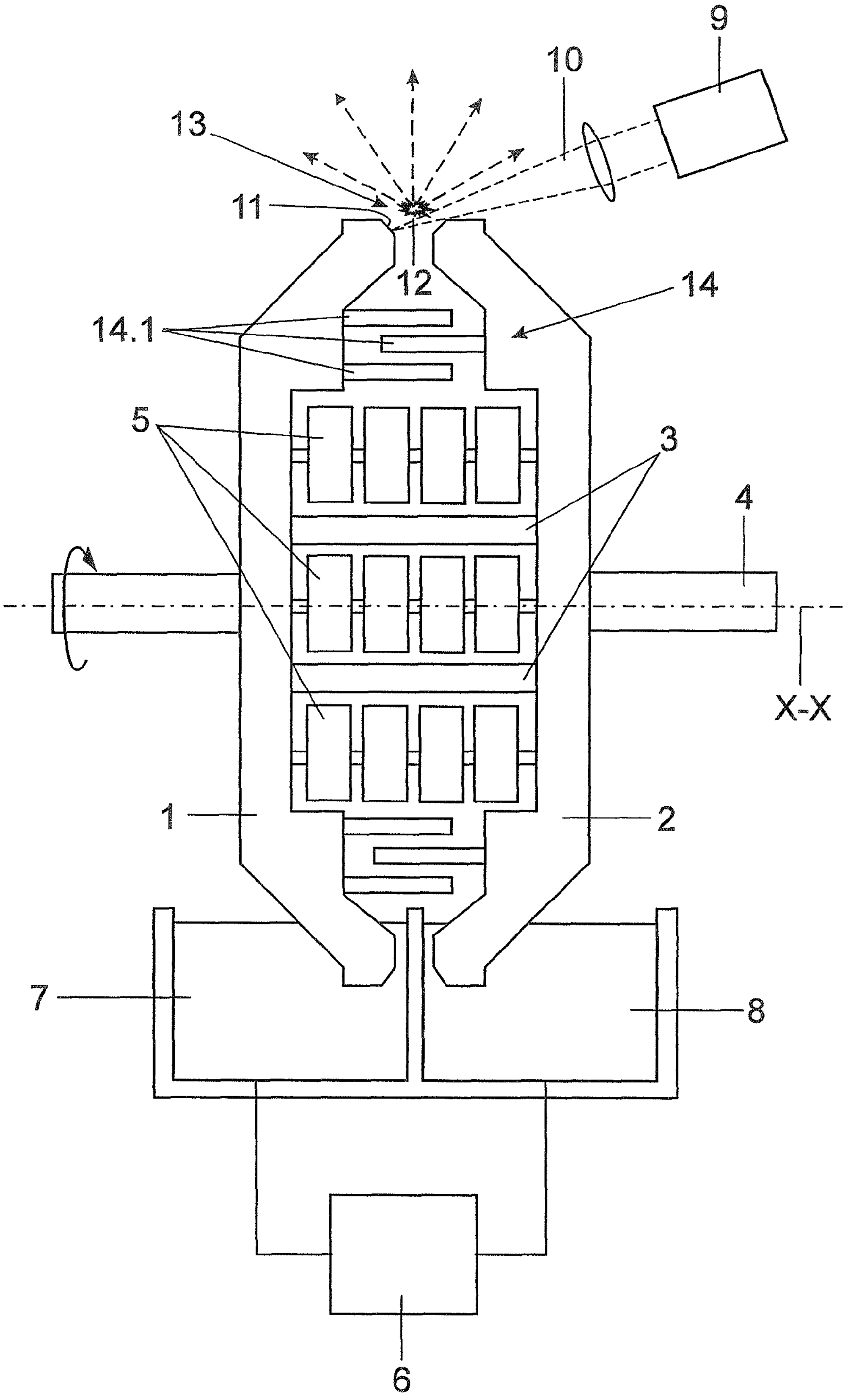
FIG. 1 shows a rotary electrode arrangement in which the electrodes are immersed in molten metal.
Figure 2:
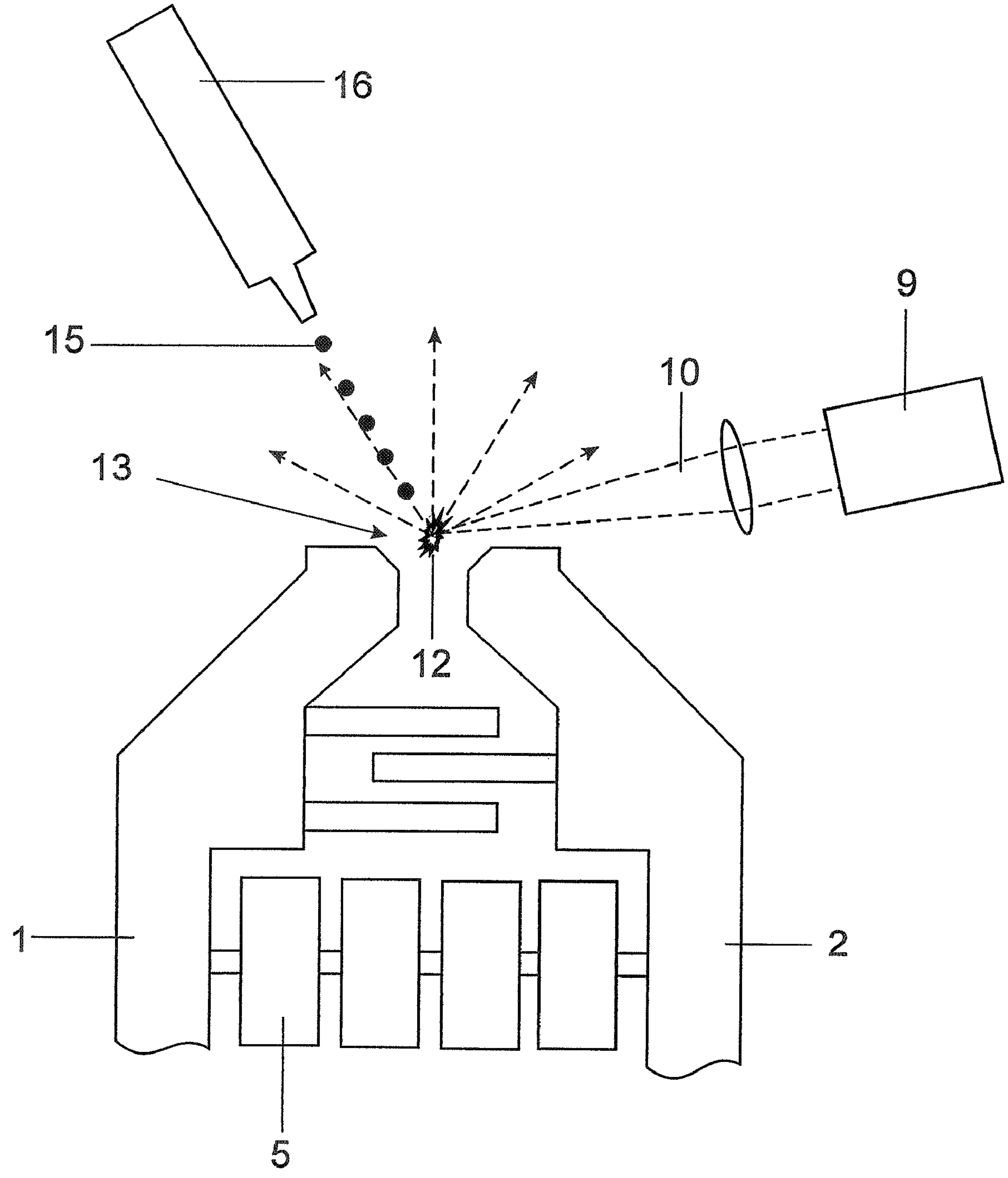
FIG. 2 shows a rotary electrode arrangement in which the starting material for the generation of radiation is introduced into the discharge area in the form of individual volumes.

In the rotary electrode arrangement shown in FIG. 1, two electrodes 1, 2 are fixedly connected to one another by means of spacers 3 comprising insulating material and are mounted so as to be rotatable around a common axis of rotation X-X extending through a shaft 4. A plurality of capacitor elements 5 which are electrically connected to the electrodes and are preferably constructed as ceramic capacitors are arranged in the free space between the electrodes 1, 2 and are charged by means of a voltage source 6 of a high-voltage power supply. The capacitor elements 5 ensure that a gas discharge can be carried out with repetition frequencies of several kHz.

In a first construction, molten metal baths 7, 8 which are separated from one another electrically and in which the electrodes 1, 2 are immersed are provided so that the molten metal which is provided as starting material for the generation of radiation is picked up as a result of the rotation of the electrodes 1, 2. This results in self-healing electrodes in which erosion of the electrodes can be countered through constant application of starting material for the generation of radiation.

Since the two melt baths 7, 8, preferably tin baths, make electrical contact with the voltage source 6, the charging of the capacitor elements 5 can take place by means of these melt baths 7, 8 and the electrodes 1, 2.

An energy beam 10 provided by an energy beam source 9 is directed to an electrode surface 11 so that starting material for the generation of radiation that is located on the surface is vaporized. The propagation of the vaporized starting material between the two electrodes 1, 2 creates the necessary conditions for the discharge of the capacitor elements 5 so that a small, hot plasma 12 is formed in the discharge area 13 as a result of the ignition of a gas discharge, which plasma 12 emits electromagnetic radiation in the preferred wavelength range.

Laser beam sources, ion beam sources and electron beam sources are particularly suitable as energy beam sources 9. It is particularly important for the operation of the rotary electrode arrangement that neither the capacitor elements 5 nor the spacers 3 are impinged upon by electrically conductive materials which can condense after the discharge at surfaces in the interior of the gas discharge source. Therefore, the rotary electrode arrangement has, in the free space between the electrodes 1, 2, a protective device in the form of a labyrinth seal 14 which comprises cylindrical rings 14.1 of metal or electrically insulating ceramic which are oriented coaxial to the axis of rotation X-X, arranged in alternating manner on the electrodes 1, 2, overlap at least partially, and surround the capacitor elements 5 and the spacers 3. When the labyrinth seal is suitably dimensioned, a long operating period is ensured without impairment by condensation.

According to a second construction of the invention, the starting material, e.g., tin, is introduced into the discharge area 13 in the form of individual volumes 5, particularly at a location at which the plasma generation is carried out in the discharge area 13 that is provided at a distance from the electrodes 1, 2. The individual volumes 15 are preferably provided as a continuous flow of droplets in dense, i.e., solid or liquid, form through an injection device 16 directed to the discharge area 13.

The energy beam 10 which is generated by the energy source 9 in a pulsed manner and which can preferably be a laser beam of a laser radiation source is directed to the location of the plasma generation in the discharge area 13 so as to be synchronized in time to the frequency of the gas discharge in order to pre-ionize one of the droplets. A beam trap, not shown, can be provided for complete absorption of any unabsorbed energy radiation.

The injection of droplets has the advantage that the distance between the plasma 12 and the electrodes 1, 2 can be increased compared to a construction according to FIG. 1 in which the starting material is evaporated from the electrode surface. This increase can lead to reduced erosion of the electrode surface. This is also advantageous when the electrodes 1, 2 run through a molten metal because eroded material can potentially lead to contamination of the gas discharge source or of the entire installation in which the gas discharge source is used.

Figure 3:
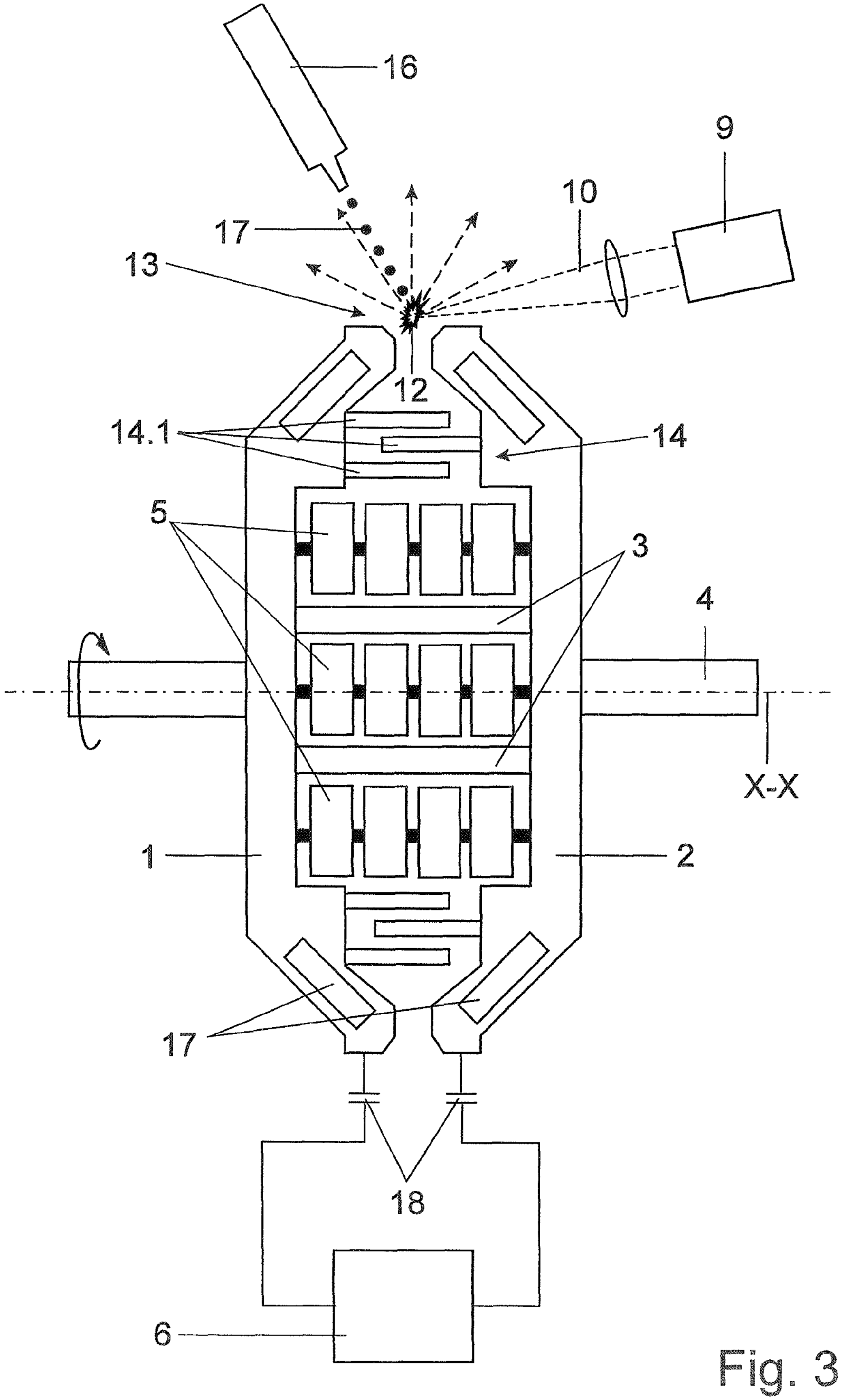
FIG. 3 shows a rotary electrode arrangement in which xenon is injected in droplet form as starting material and in which power is supplied by means of sliding contacts.

A contamination problem of this kind in connection with metal emitters, particularly with tin, can be circumvented in that droplets of frozen xenon are introduced as individual volumes into the discharge area 13 according to FIG. 3 and are vaporized by laser radiation.

Since the erosion of the electrode surface by the plasma 12 depends upon the temperature of the electrodes 1, 2, the latter can have interior cooling ducts 17 through which coolant, e.g., water, flows for direct cooling. When the coolant is pressed through the cooling ducts 17 at high pressure, the efficiency of cooling is increased, particularly also through the considerable increase in the boiling temperature of the coolant.

The electrical energy required for the gas discharge can be supplied by the voltage source 6 to the capacitor elements 5 in different ways. According to FIG. 3, for example, the electrodes 1, 2 are electrically connected to the voltage source 6 by sliding contacts 18.

Figure 4:
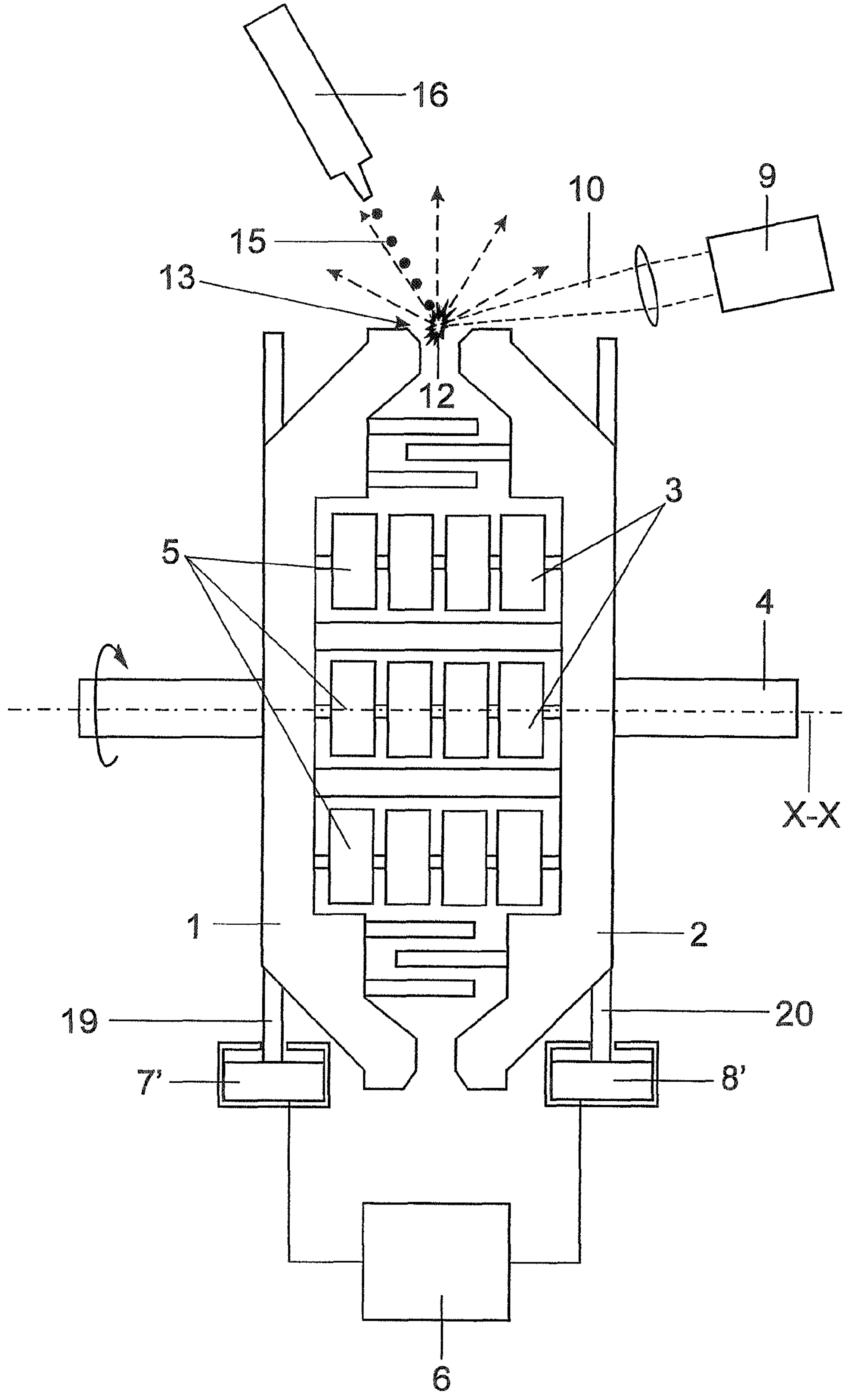
FIG. 4 shows a rotary electrode arrangement in which xenon is injected in droplet form as starting material and in which power is supplied by means of electrically insulated baths of molten metal.

In another construction according to FIG. 4, in which xenon droplets are again injected into the discharge area 13 as individual volumes 15, the power supply to the capacitor elements 5 is carried out via electrically insulated molten metal baths 7', 8', preferably tin baths or baths of other low-melting metals such as gallium. However, in contrast to the construction according to FIG. 1, the electrodes 1, 2 are not immersed directly in the molten metal; rather, this operation is taken over by annular-disk-shaped immersion elements 19, 20 which comprise electrically conductive material and enclose the electrodes 1, 2 and are in electrical contact therewith. The immersion elements 19, 20 are so deigned with respect to shape and size so as to prevent evaporation of the metal picked up by them. In particular, there is no direct line of sight from the wetted surface of the immersion elements 19, 20 to the plasma 12 so that erosion is prevented.

Also when injecting xenon droplets, a solution of the kind described above makes it possible to supply current to the capacitor elements 5 without wear and without resulting in metal deposits in or outside the gas discharge source.

Further, when using low-melting metals, baths of molten metal have the advantage that they can be used under certain circumstances to cool the electrodes which, as a result of the high electrical power applied, can often reach much higher temperatures than are needed for the operation of the melt baths. This excess heat can be removed by cooling the melt baths.

Figure 5:
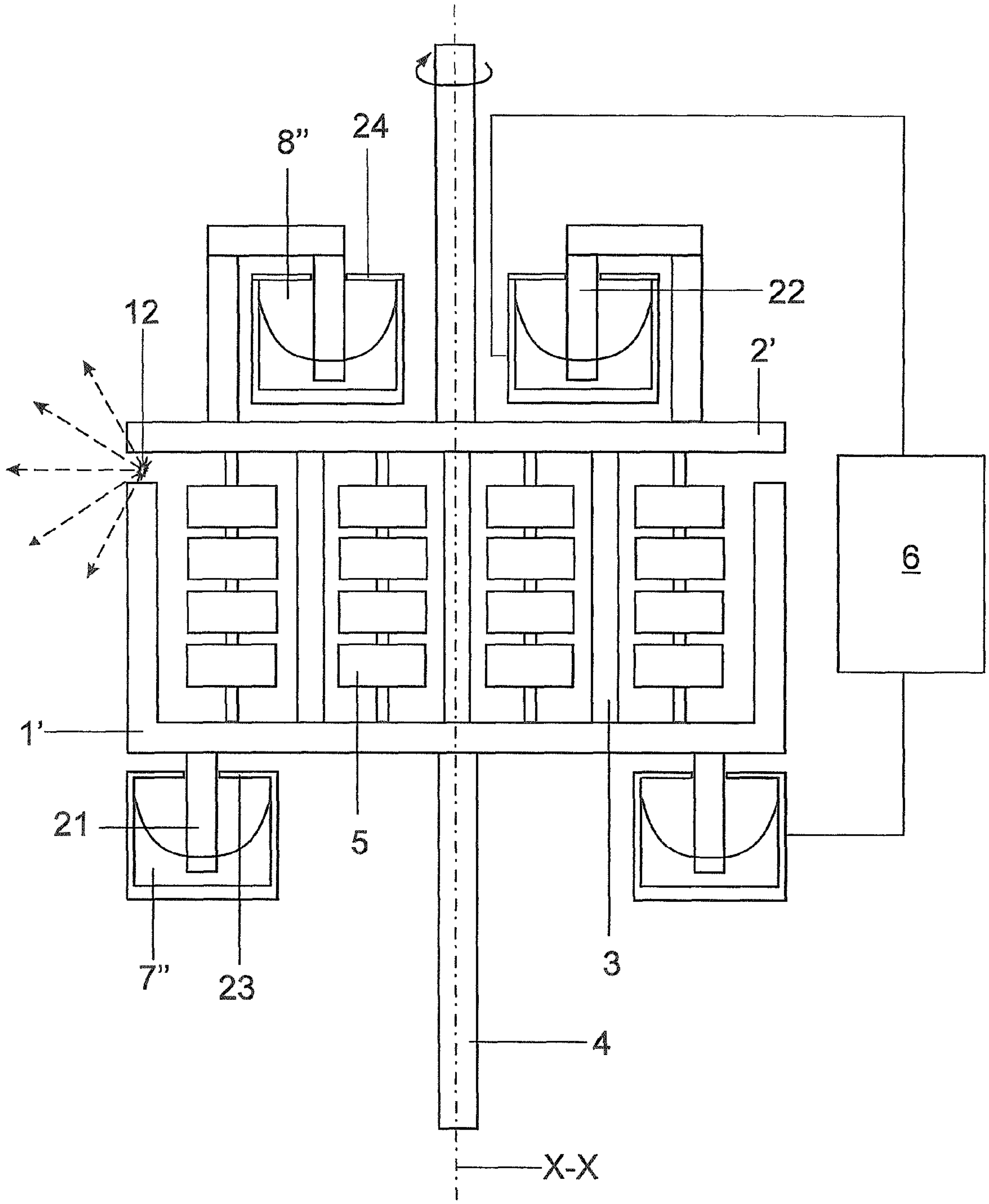
FIG. 5 shows a variant of the construction according to FIG. 4, wherein the axis of rotation of the rotary electrode arrangement is arranged vertically.

In a differently constructed variant of the construction according to FIG. 4, the axis of rotation X-X corresponding to FIG. 5 is arranged vertically. Electrically separated melt baths 7", 8" of a molten metal, preferably tin, are provided for both electrodes 1', 2' and surround the shaft 4 coaxially, the electrodes 1', 2' penetrating therein with cylindrical-ring-shaped electric contact elements 21, 22. The melt baths 7", 8" are provided with covers 23, 24 which leave open only a small gap to the contact elements 21, 22 in order to minimize the evaporation of the molten metal.

Further, the melt baths 7", 8" serve at the same time to carry off heat that is deposited in the electrodes 1', 2' due to the discharge. For this reason, the melt baths 7", 8" are suitably cooled in a manner not shown.

In this case also, the emitter material needed for the generation of the plasma 12 can either be introduced into the discharge area in the form of droplets, where it is vaporized by an energy beam, or it is applied to the surface of one of the electrodes 1', 2' in a suitable manner and introduced into the discharge area from there by an energy beam.

Figure 6:
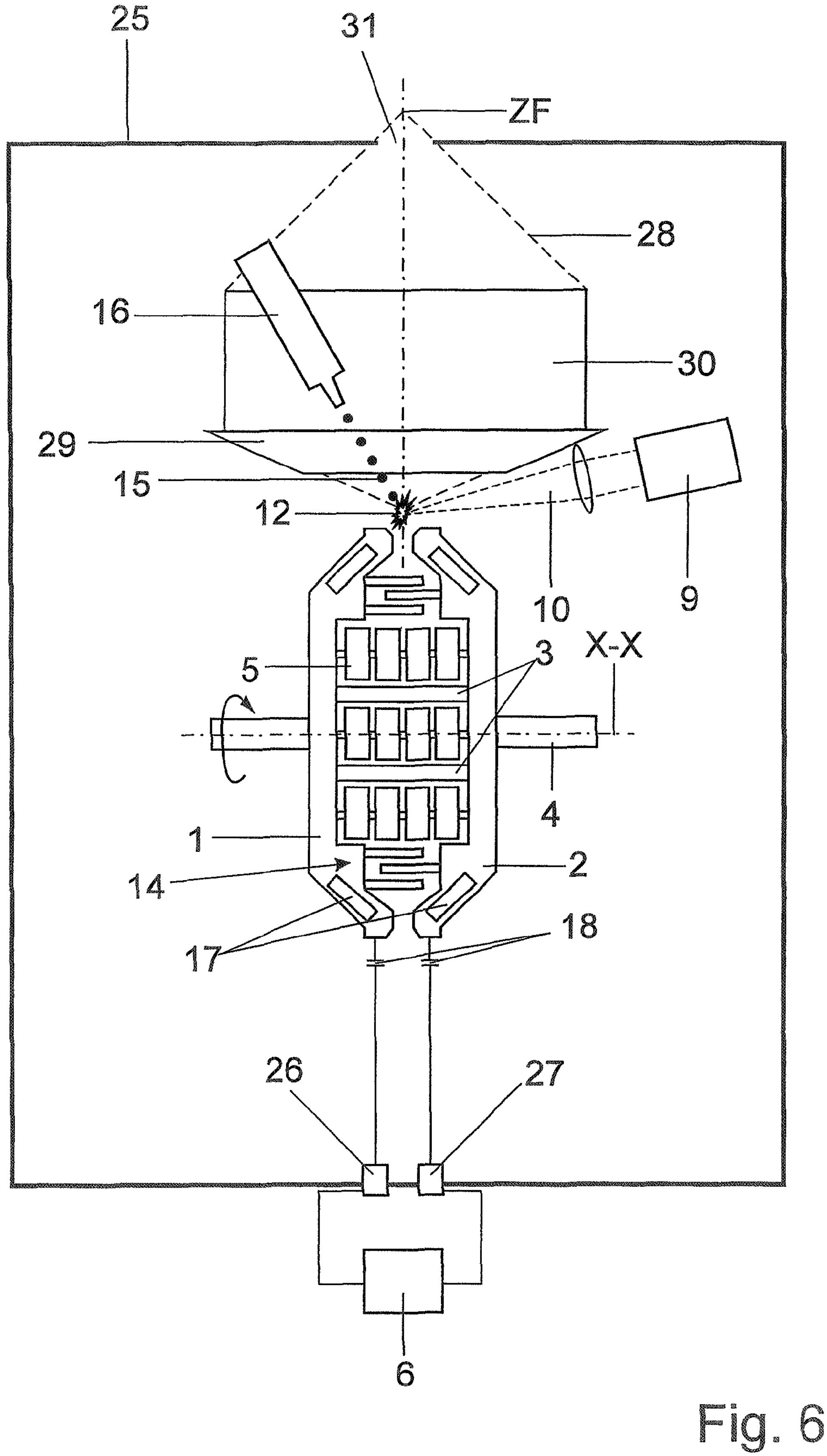
FIG. 6 shows a gas discharge source with a rotary electrode arrangement according to the invention.

The fact that the essential component parts of the gas discharge source shown additionally in FIG. 6 is shown only for the construction according to FIG. 3 should not imply any limitation. Analogously, these component parts can, of course, also be found in the other constructions.

The rotary electrode arrangement according to the invention is accommodated in a discharge chamber 25 formed as a vacuum chamber from which the electric connection to the voltage source 6 is carried out by means of electric vacuum feedthroughs 26, 27.

After passing through a debris protection device 29, the radiation 28 emitted by the hot plasma 12 reaches collector optics 30 which direct the radiation 28 to a beam outlet opening 31 in the discharge chamber 25. Imaging the plasma 12 by means of the collector optics 30 generates an intermediate focus ZF which is localized in or in the vicinity of the beam outlet opening 31 and which serves as an interface to exposure optics in a semiconductor exposure installation for which the gas discharge source, which is preferably constructed for the EUV wavelength range, can be provided.

While the foregoing description and drawings represent the present invention, it will be obvious to those skilled in the art that various changes may be made therein without departing from the true spirit and scope of the present invention.

What is claimed:

1. An arrangement for generating radiation by a gas discharge comprising:

a discharge chamber having a discharge area for the gas discharge for forming a plasma that emits the radiation from a starting material and an emission opening for the generated radiation;

a first electrode and a second electrode, said electrodes being mounted so as to be rotatable;

a high-voltage power supply for generating high-voltage pulses between the two electrodes;

said electrodes being rigidly connected to one another at a distance from one another and being mounted so as to be rotatable around a common axis;

capacitor elements of said high-voltage power supply being arranged in a free space formed by the mutual distance; and said electrodes being electrically connected to said capacitor elements and to a voltage source for charging the capacitor elements.

2. The arrangement according to claim 1, wherein the electrodes are immersed in baths of a molten metal which are electrically separated from one another, so that the surface of the electrodes is wetted by the metal during the rotation of the electrodes.

3. The arrangement according to claim 2, wherein the metal bath is a tin bath.

4. The arrangement according to claim 2, wherein the metal bath is a lithium bath or gallium bath.

5. The arrangement according to claim 1, wherein the electrodes are in electrical contact with immersion elements which are oriented coaxial to the axis of rotation and which penetrate into molten metal baths which are electrically separated from one another, wherein the electrical connection of the electrodes to the voltage source is carried out by the metal bath.

6. The arrangement according to claim 3, wherein the electrical connection of the electrodes to the voltage source is carried out by melt bath.

7. The arrangement according to claim 6, wherein an injection device is directed to the discharge area, which injection device supplies a series of individual volumes of the starting material serving to generate radiation and injects them into the discharge area at a distance from the electrodes.

8. The arrangement according to claim 4, wherein an injection device is directed to the discharge area, which injection device supplies a series of individual volumes of the starting material serving to generate radiation and injects them into the discharge area at a distance from the electrodes.

9. The arrangement according to claim 5, wherein an injection device is directed to the discharge area, which injection device supplies a series of individual volumes of the starting material serving to generate radiation and injects them into the discharge area at a distance from the electrodes.

10. The arrangement according to claim 1, wherein an injection device is directed to the discharge area, which injection device supplies a series of individual volumes of the starting material serving to generate radiation and injects them into the discharge area at a distance from the electrodes, and in that the electrical connection of the electrodes to the voltage source is carried out by sliding contacts.

11. The arrangement according to claim 7, wherein the individual volumes injected into the discharge area are formed as liquid or solid droplets.

12. The arrangement according to claim 11, wherein the droplets comprise metal material.

13. The arrangement according to claim 12, wherein tine or lithium is provided as metal material.

14. The arrangement according to claim 11, wherein the droplets comprise liquid or frozen xenon.

15. The arrangement according to claim 3, wherein the molten metal picked up by the electrodes is provided as starting material for the generation of radiation.

16. The arrangement according to claim 10, wherein an energy beam provided by an energy beam source is directed to the starting material for the generation of radiation so that an at least partial pre-ionization of the starting material is carried out.

17. The arrangement according to claim 16, wherein the energy beam source is a laser beam source.

18. The arrangement according to claim 16, wherein the energy beam source is an electron beam source.

19. The arrangement according to claim 16, wherein the energy beam source is an ion beam source.

20. The arrangement according to claim 1, wherein a device for preventing deposits of material arranged between the discharge area and the capacitor elements is accommodated in the free space between the electrodes.

21. The arrangement according to claim 20, wherein the device is a labyrinth seal comprising cylindrical rings which are oriented coaxial to the axis of rotation, arranged in an alternating manner at the electrodes, overlap at least partially, and surround the capacitor elements.

22. The arrangement according to claim 21, wherein the cylindrical rings comprise metal.

23. The arrangement according to claim 21, wherein the cylindrical rings comprise electrically insulating ceramic material.

24. The arrangement according to claim 1, wherein cooling ducts are arranged in the electrodes.

* * * * *